US012788994B2

(12) United States Patent
McIntosh

(10) Patent No.: US 12,788,994 B2
(45) Date of Patent: Nov. 10, 2026

(54) IMPLANTABLE PULSE GENERATOR

(71) Applicant: BIOTRONIK SE & Co. KG, Berlin (DE)

(72) Inventor: David McIntosh, Wilson, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 255 days.

(21) Appl. No.: 18/712,367

(22) PCT Filed: Nov. 21, 2022

(86) PCT No.: PCT/EP2022/082585

§ 371 (c)(1),
(2) Date: May 22, 2024

(87) PCT Pub. No.: WO2023/094313

PCT Pub. Date: Jun. 1, 2023

(65) Prior Publication Data

US 2025/0010082 A1 Jan. 9, 2025

Related U.S. Application Data

(60) Provisional application No. 63/282,222, filed on Nov. 23, 2021.

(30) Foreign Application Priority Data

Dec. 8, 2021 (EP) .................................... 21213000

(51) Int. Cl.
*A61N 1/372* (2006.01)
*A61N 1/378* (2006.01)
(Continued)

(52) U.S. Cl.
CPC ....... *A61N 1/37223* (2013.01); *A61N 1/3787* (2013.01); *H02J 50/12* (2016.02); *H02J 50/80* (2016.02); *H04B 5/79* (2024.01)

(58) Field of Classification Search
CPC ... A61N 1/37223; A61N 1/3787; H02J 50/80; H02J 50/12; H04B 5/79
See application file for complete search history.

(56) References Cited

U.S. PATENT DOCUMENTS 9,694,192 B2 7/2017 Vansickle et al.
10,886,761 B1 1/2021 Schobben et al.
(Continued)

OTHER PUBLICATIONS

International Search Report and Written Opinion for PCT/EP2022/082585 mailed Jan. 24, 2023, 16 pages.

*Primary Examiner* — Benjamin J Klein
*Assistant Examiner* — Thien Jason Tran
(74) *Attorney, Agent, or Firm* — FBT Gibbons LLP

(57) ABSTRACT

An implantable pulse generator (IPG) for neurostimulation includes a recharging unit with a rechargeable battery adapted to receive energy from a separate charger utilizing inductive power transfer from a primary coil of the charger to a secondary coil of the recharging unit. The IPG includes a processing unit. The recharging unit is adapted to communicate information from the IPG to the charger utilizing capacitive load shift keying (C-LSK) and resistive load shift keying (R-LSK). The processing unit is adapted to control dynamical selection of C-LSK or R-LSK for communication of pre-defined information or to control both C-LSK and R-LSK for communication of pre-defined information in a pre-defined sequence dependent on values of the electric circuitry of the recharging unit or dependent on the type of information communicated to the charger. A system includes the IPG, a charger, and a neurostimulation device.

15 Claims, 2 Drawing Sheets

Figure 1:
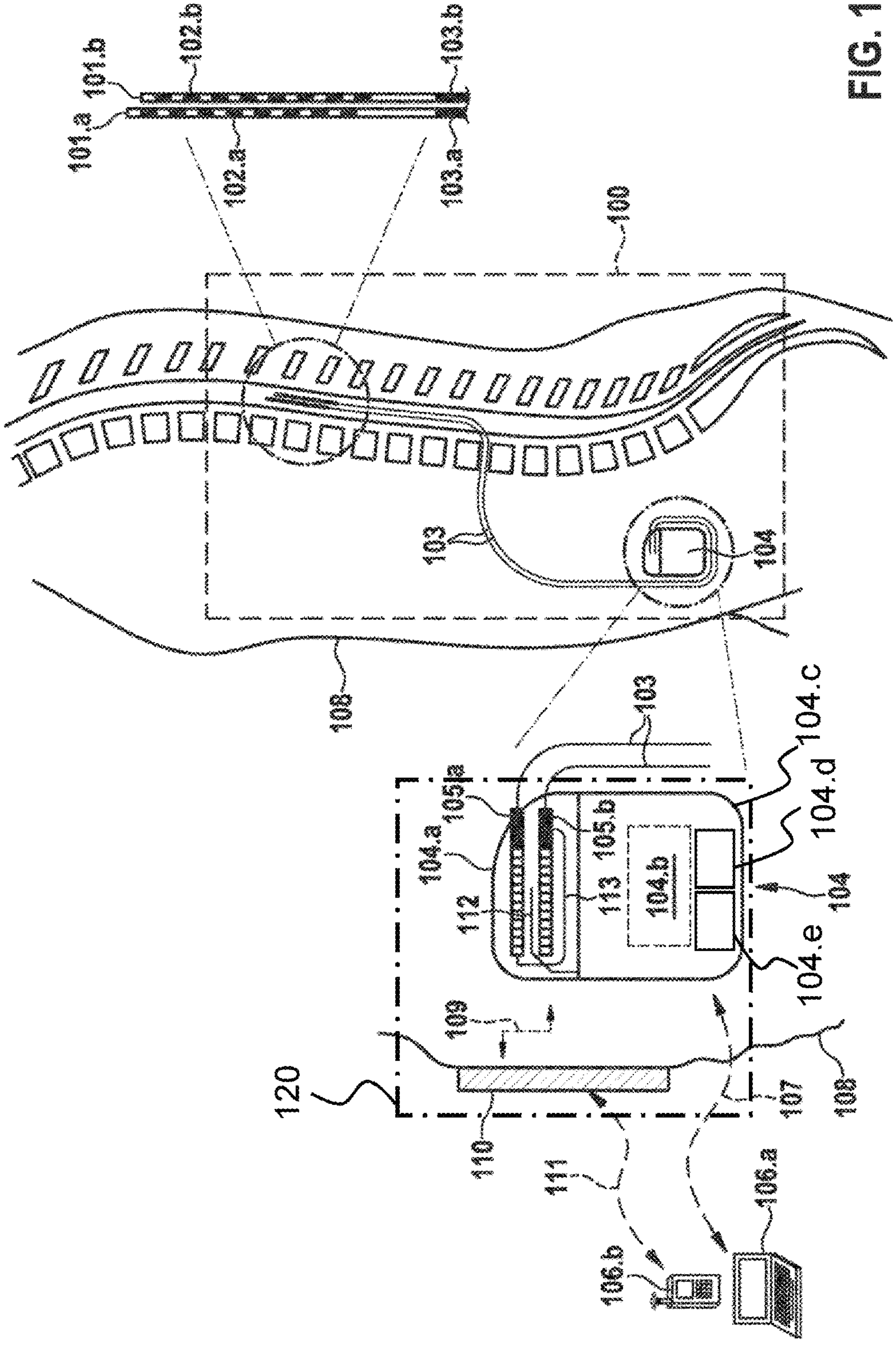

(51) Int. Cl.
*H02J 50/12* (2016.01)
*H02J 50/80* (2016.01)
*H04B 5/79* (2024.01)

(56) References Cited

U.S. PATENT DOCUMENTS

| | | | | |
|---|---|---|---|---|
| 2010/0305663 | A1* | 12/2010 | Aghassian | A61N 1/37223 607/61 |
| 2013/0123881 | A1 | 5/2013 | Aghassian | |
| 2014/0200631 | A1 | 7/2014 | Carbunaru et al. | |
| 2017/0125892 | A1* | 5/2017 | Arbabian | H04B 5/26 |
| 2023/0239005 | A1* | 7/2023 | Yakovlev | H04B 5/45 375/256 |

* cited by examiner

IMPLANTABLE PULSE GENERATOR

The invention is directed to an implantable pulse generator (IPG) for neurostimulation of a patient's body and a respective method for operating same as well as to a neurostimulation device comprising such IPG and a system comprising the IPG and a charger, in particular wireless power transfer (WPT) charger.

Neurostimulation devices are used to deliver electrical stimulation therapy to a patient's body 15 to various tissue sites to treat a variety of symptoms or conditions such as chronic pain, Parkinson's disease, epilepsy, urinary or fecal incontinence, sexual dysfunction, obesity or gastroparesis. Such devices usually deliver electrical stimulation therapy in form of pulses via one or more leads that comprise electrodes located proximate to target locations associated with the brain, the spinal cord, pelvic nerves, peripheral nerves, or the gastrointestinal tract of the patient. Hence, electrical simulation may be used in different therapeutic applications, such as deep brain stimulation (DBS), spinal cord stimulation (SCS), pelvic stimulation, gastric stimulation, or peripheral nerve stimulation (PNS). The neurostimulation device comprises an implantable pulse generator (IPG) generating the electrical pulses for neurostimulation and electrode leads which are connected to the IPG.

It is known to use wireless power transfer (WPT) in order to recharge a battery of a transcutaneously located IPG using a separate charger which is external from the patient's body. In particular WPT refers here to inductive or resonant magnetic coupling. Often the charger is a cable-less and hand-held unit, with its own secondary battery (the Power Source), which may be placed over the IPG site to inductively (or by resonant magnetic coupling) transfer power to the battery of the IPG.

Further, such system can be used to provide unidirectional or bidirectional communication from the IPG to the charger and/or vice versa utilizing the effect of backscatter modulation which is also referred to as Load Shift Keying (LSK). Basically, the system uses amplitude modulation of the charger side coil's current as the means for communication. Amplitude modulation is a simple means for communication. Demodulation is provided on the charger side.

One fundamental performance metric of an amplitude modulation communication detector is how much change in the amplitude is observed when the LSK communication is ongoing: the modulation depth. It was found that a higher modulation depth causes a much lower bit error rate during communication for a given signal-to-noise condition. While static WPT system can be optimally tuned for optimal modulation depth, dynamic systems with an implanted IPG and a charger that is misaligned from the IPG exhibit variability in the resonant frequency of the WPT system and thereby in the amplitude modulation depth.

There are known systems that provide dynamic tuning methods which are constantly changing the excitation frequency to track the new resonant frequency requiring a quite sophisticated algorithm to search and identify the resonant frequency wherein the algorithm needs to be stable and responsive.

Further, from a patient perspective, they have to align their charger to the IPG for hours and on a daily basis. Over some volume of displacements between the charger and IPG, there are so-called "null" points where the modulation depth is poor and communication performance is reduced. In some cases, the null point may even occur in the perfectly aligned case, resulting in requiring the patient to purposefully misalign his/her charger from the IPG. It further was identified from some experiments that each patient has a different set of null points depending on the IPG depth, the angle of the IPG and the relative resonant frequency tuning tolerance of the charger and IPG.

Accordingly, there is a desire to provide an IPG and a respective method which easily and cost-effectively provides a reliable LSK communication with the charger.

The above objective is solved by an implantable pulse generator (IPG) for neurostimulation of a patient's body with the features of claim 1, a system comprising the IPG and a charger, in particular a WPT charger, with the features of claim 6, a neurostimulation device with the features of claim 8, a method for operating such IPG with the features of claim 9 and a method for operating such system with the features of claim 14.

In particular, the IPG for neurostimulation of a patient's body has a recharging unit with a rechargeable battery adapted to receive energy from a separate charger utilizing inductive or resonant magnetic power transfer from a primary coil of the charger to a secondary coil of the recharging unit, wherein the IPG further comprises a processing unit, wherein the recharging unit is adapted to communicate information from the IPG to the charger utilizing capacitive load shift keying (C-LSK) and resistive load shift keying (R-LSK), wherein the processing unit is adapted to control dynamical selection of either C-LSK or R-LSK for communication of a pre-defined information and/or to control usage of both C-LSK and R-LSK for communication of a predefined information in a pre-defined sequence dependent on an actual measured value of at least one parameter of the electric circuitry of the recharging unit and/or dependent on the type of information which is to be communicated to the charger. C-LSK may purposefully add shunt capacitance to achieve detuning, while R-LSK may purposefully add a load (resistive or current sink). Advantage of C-LSK is that it is theoretically lossless, while R-LSK requires power dissipation.

The implantable pulse generator (IPG) generates electrical pulses for neurostimulation. Further, the IPG comprises at least one connector for connecting at least one electrode lead which may be a percutaneous lead or a surgical lead. The at least one electrode lead transmits the generated electrical pulses by their electrode(s) to the target within the patient's body in order to provide neurostimulation therapy. The IPG may be adapted to provide electrical simulation used in different therapeutic applications, for example deep brain stimulation (DBS), spinal cord stimulation (SCS), pelvic stimulation, gastric stimulation, sacral nerve stimulation (e.g. in case of incontinence) or peripheral nerve stimulation (PNS).

The IPG comprises the electrical circuitry, for example comprising an application specific integrated circuit (ASIC), for providing electrical stimulation output and a battery, wherein the electrical circuitry, the battery and the at least one lead with the electrodes are electrically interconnected with each other. The IPG further comprise a processing unit and may comprise a memory unit for storing data and/or a communication module for communication with an external computer or programmer. The processing unit is regarded as a functional unit of the remote device that interprets and executes instructions comprising an instruction control unit and an arithmetic and logic unit. The processing unit, memory unit and/or communication module may be electrically interconnected with the electrical circuitry and the battery of the IPG as well as with the at least one electrode lead. All elements of the IPG are contained within a hermetically sealed housing.

The patient may receive battery status information when using a patient remote which may be in communication connection with the IPG. In addition, if the battery is low, the patient may receive a warning that therapy may be shut off soon. When the battery state of charge is critically low, the IPG disables therapy and beacons via RF to the patient remote that it is is time to recharge the IPG.

The recharging unit of the IPG facilitates recharging of the battery and for that comprises the secondary coil, the rechargeable battery and part of the electrical circuitry of the IPG. The recharging unit is electrically connected to the processing unit. The processing unit controls operation of the recharging unit. The recharging unit provides energy to the battery by inductive wireless power transfer (WPT) from the external charger comprising the primary coil. Depending on the therapy settings, the IPG recharge interval varies, e.g., from a single day to several weeks. One recharging session may, for example, take 15 min to 2 hours, in particular 30 min to 90 min. The charger may be a cable-less and hand-held unit and may comprise its own secondary battery (the power source). Alternatively, the charger may be connected with the mains-powered power supply. The IPG may be movable and may be placed over the IPG site at the patient's body to inductively transfer power to the battery of the IPG. The charger may be held in place over the IPG using a patient affixation (e.g. a belt or adhesive) during recharging.

The charger, when not in use, may be powered from a mains wall adapter, e.g. an AC/DC mains wall adapter, which may directly plug into the charger. The charger may include a user interface, for example a push-button, which is used to activate the recharging function.

In order to transmit feedback to the charger for positioning assistance and in order to maintain an efficient and safe charging link, the IPG is further adapted to unidirectionally communicate information to the charger utilizing capacitive load shift keying (C-LSK) and resistive load shift keying (R-LSK). Accordingly, the recharging unit provides respective circuitry for both, C-LSK and R-LSK.

The communication scheme of LSK operates directly on the power transfer excitation signal (carrier) from the charger. The result is an amplitude modulation (AM) of the charger's driving impedance which contains information. The backscatter communication is only possible when the carrier signal is present, i.e. when power is being transferred from the is charger to the IPG. The charger demodulates and digitally restores the information which is contained in current and/or voltage waveforms on the resonant tank of the charger. A technical explanation is that the modulated impedance on the IPG side is reflected unto the charger resonant tank.

An important aspect of the recharging unit is to adapt the modulation depth to the actual charging conditions of the system comprising the recharging unit of the IPG and the charger, by switching the LSK mode (C-LSK and R-LSK) used for information transmission to the charger. Alternatively or additionally, the information may be provided to the charger in a pre-defined sequence by both LSK modi. By the latter embodiment, the chances are increased that the intended information is received by the charger. Accordingly, the processing unit controls dynamic selection of either C-LSK or R-LSK for communication of a pre-defined information and/or to control usage of both C-LSK and R-LSK for communication of a pre-defined information in a pre-defined sequence. The processing unit provides this/these controlling function(s) dependent on an actual measured value of at least one parameter of the electric circuitry of the recharging unit and/or dependent on the type of information which is to be communicated to the charger. The modulation depth is changed by switching the LSK mode because for example in a series-series resonant network which is part of the electric circuitry of the recharging unit R-LSK exhibits a maximum modulation depth at the resonant frequency whereas C-LSK exhibits a minimum modulation depth at the resonant frequency. The resonant frequency changes, for example, with the spatial arrangement of IPG and charger. Accordingly, modulation depth may be increased by switching from one LSK mode to the other. In the case of a "last gasp" shutdown situation of the IPG, when the IPG detects a fault and requests the charger to shut off immediately, a respective information may be sent several times to the charger using both LSK modi, for example 3 times by C-LSK and, after that, 3 times by R-LSK to improve the reliability of the transmission of this information to the charger.

In one embodiment, the at least one parameter of the electric circuitry of the recharging unit is the DC link voltage and/or the battery current (being the current for recharging the battery and powering the remainder of the IPG). The DC link voltage is the voltage measurable at the electric circuitry of the IPG that is used to power the IPG (i.e. the pulse generating unit) is while at the same time recharging the battery.

The recharging unit of the IPG may provide fast messages/information (i.e. messages with a repetition rate in the area of 10th of a second) to the charger which are used by the charger for maintaining a target supply voltage or current on the IPG using a closed-loop control system. Less frequently, the recharging unit of the IPG may provide messages/information related to safety (IPG temperature, recharging rate, battery voltages) which are used by the charger to validate that recharging conditions are safe to maintain recharging. In addition, it may use those messages/information to improve the control loop performance. Finally, the recharging unit of the IPG may infrequently and asynchronously have to convey a special message/information to the charger which may be generated based on a signal of the processing unit of the IPG. The transmitted message/information is extracted by the charger and interpreted, wherein afterwards a respective reaction of the charger (e.g. shut off, adaption of the recharging electromagnetic field, for example as a part of the closed loop control) is initiated.

By the above-described recharging unit a highly power efficient communication link is provided that leads to minimizing parasitic eddy-current based heating of the IPG can, IPG battery and other conductors and that realizes patient safety. In addition, the highly efficient link may reduce the charger's power source size. Further, it supports a short and predictable charging session that helps ensuring that the patient charges frequently and comfortably, providing uninterrupted delivery of therapy. A highly efficient communication link is ensured by the above-described dynamic adjustment of the charger's operating point based on the present conditions. Further, the magnetic and electrical design of the charging coils (first coil of the charger, second coil of the recharging unit) may further increase efficiency of the communication link.

Accordingly, the above objective is further solved by a system comprising the IPG and the separate charger having the primary coil for providing inductive power transfer to the secondary coil.

In steady charging state, the charger operates in a closed loop with the goal of maintaining a is DC link voltage on the IPG within a target window under varying load (e.g. charge rates) and charger-IPG misalignment in order to recharge the battery of the recharging unit of the IPG. The charger may use backscatter messages sent by the IPG as the feedback for regulation of the loop. In addition, informational, suspension and termination messages may be sent from the IPG to the charger. When the charger receives a valid message it may be required to take an action by the charger, e.g. turn off charging power or activate a user-viewable indicator.

The charger may realize at least one of the following safety principles:

- If the charger has not received feedback communication from the IPG, the charger shuts off after a timeout.
- If the Charger receives suspension/terminate messages from the IPG, the charger shall shut off without delay.
- The charger requires patient action to turn on power transfer (i.e. no persistent auto-retry is established).
- If the charging efficiency is out of range (of a window), patient is alerted and charging terminates.

In one embodiment, the IPG further comprises a measurement unit, comprising, for example, a voltmeter and/or an ammeter, adapted to determine the actual value of the at least one parameter of the electric circuitry and to transmit the measured actual value to the processing unit. Additionally, the measurement unit may comprise a temperature sensor determining, for example, the temperature of the battery and/or the temperature of the recharging unit.

In one embodiment, the selection of C-LSK comprises switching on a capacitive load connected in parallel to the secondary coil and switching off a resistive load connected in parallel to the secondary coil or at the DC link. This is an easy and cost-effective way to realize C-LSK. The switching may be triggered by the processing unit.

In one embodiment, the selection of R-LSK comprises switching off the capacitive load connected in parallel to the secondary coil and switching on the resistive load, e.g. a resistor or a current sink, connected in parallel to the secondary coil or at the DC link. This is an easy and cost-effective way to realize R-LSK. The switching may be triggered by the processing unit.

In both above embodiments both, the capacitive load and the resistive load are connected in series with a switch which is opened or closed by the processing unit if the respective load is to be switched off or on, respectively.

In one embodiment, the charger is adapted to operate the primary coil at a constant frequency, for example in a frequency range of 50 kHz to 500 kHz.

In one embodiment, the charger is adapted to use the same amplitude modulation detection method for both R-LSK and C-LSK modes of operation.

The above objective is further solved by a neurostimulation device, for example an SCS device, comprising the above described IPG and at least one electrode lead connected to the IPG.

Additionally, the above objective is solved by a method for operating an implantable pulse generator (IPG) for neurostimulation of a patient's body having a recharging unit with a rechargeable battery and a processing unit, wherein the recharging unit receives energy from a separate charger utilizing inductive power transfer from a primary coil of the charger to a secondary coil of the recharging unit, wherein the recharging unit communicates information from the IPG to the charger utilizing capacitive load shift keying (C-LSK) and resistive load shift keying (R-LSK) by the recharging unit, wherein the processing unit controls a dynamical selection of either C-LSK or R-LSK for communication of a pre-defined information and/or controls a usage of both C-LSK and R-LSK for communication of a pre-defined information in a pre-defined sequence dependent on an actual measured value of at least one parameter of the electric circuitry of the recharging unit and/or dependent on the type of information which is to be communicated to the charger.

The advantages of the method for operating the IPG and below embodiments of the method is are already explained above in connection with the IPG and the system comprising the IPG and the charger and their embodiments. It is therefore referred to the above explanation.

In one embodiment of the method, the at least one parameter of the electric circuitry of the recharging unit is the DC link voltage and the battery current.

In one embodiment of the method, the IPG further comprises a measurement unit which determines the actual value of the at least one parameter of the electric circuitry and transmits the measured actual value to the processing unit.

In one embodiment of the method, the selection of C-LSK comprises switching on a capacitive load connected in parallel to the secondary coil and switching off a resistive load connected in parallel to the secondary coil.

In one embodiment of the method, the selection of R-LSK comprises switching off the capacitive load connected in parallel to the secondary coil and switching on the resistive load connected in parallel to the secondary coil.

The above objective is further solved by a method for operating a system comprising the IPG and the charger comprising the steps of the method of any of the claims 8 to 12, wherein the charger comprises the primary coil and provides inductive power transfer to the secondary coil of the recharging unit of the IPG.

In one embodiment of the method, the primary coil operates at a constant frequency.

Figure 2:
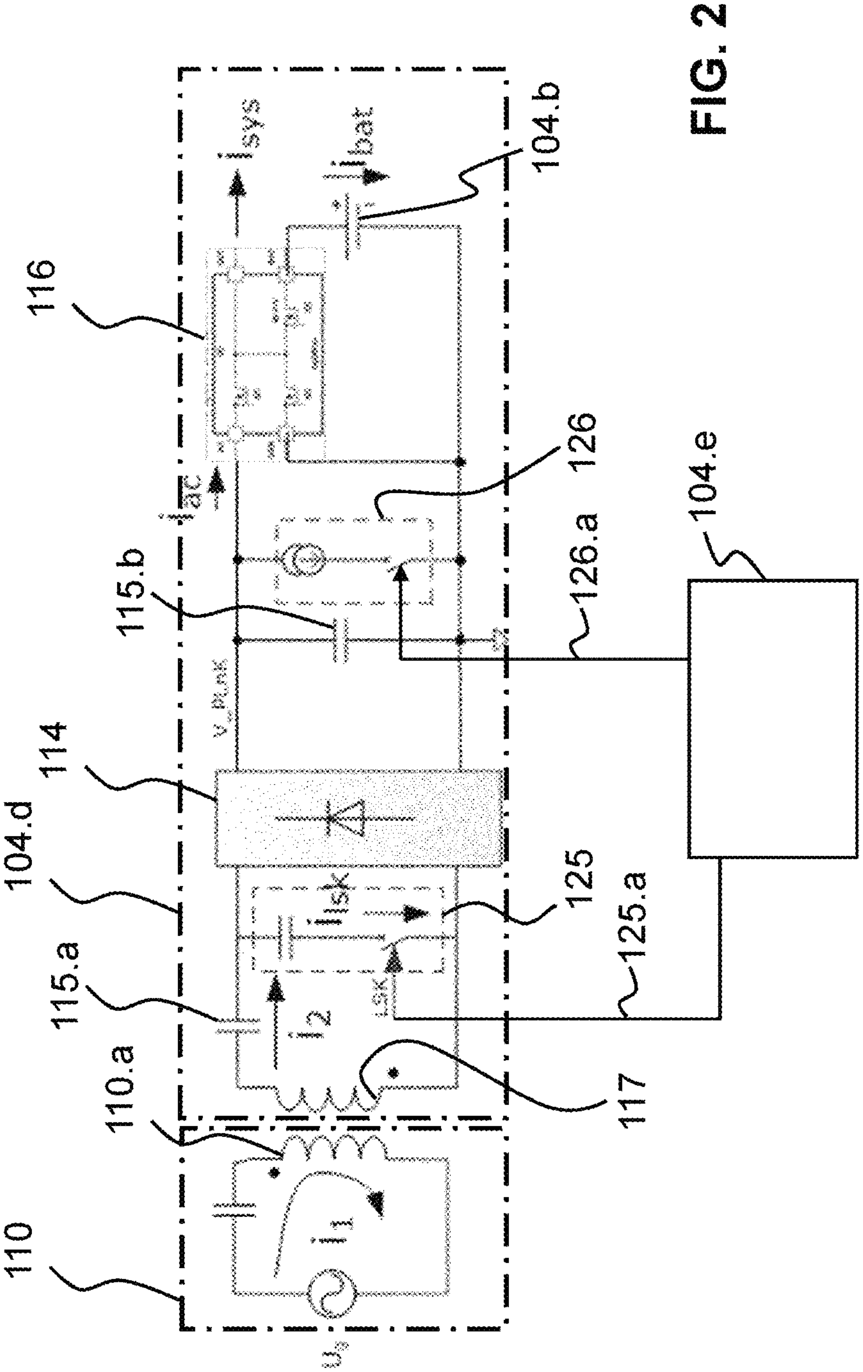

Furthermore, detailed embodiments and features of the present invention will be described below with reference to schematic drawings, wherein FIG. 1 shows an embodiment of an implantable pulse generator of an SCS device within a patient's body and an embodiment of a charger and FIG. 2 shows a wiring diagram of the charger of FIG. 1 and of an embodiment of a recharging unit of the IPG shown in FIG. 1.

FIG. 1 illustrates an implantable spinal cord stimulation (SCS) device 100 as an embodiment of a neurostimulation device which includes an embodiment of an implantable pulse generator (IPG) 104 and electrode-bearing leads 101.*a* and 101.*b*. Further, an external charger 110 is shown. The external charger 110 and the IPG 104 form an embodiment of a system 120. The leads 101.*a* and 101.*b* are shown percutaneously implanted into a targeted location in a patient's epidural space, though they could be implanted elsewhere, and the leads 101 may have a configuration different from that shown (e.g., they may be replaced by paddle leads or other types of SCS leads). The distal portions of the leads 101.*a* and 101.*b* are each shown bearing octal (eight) electrodes 102.*a* and 102.*b*, though other numbers of electrodes 102 are possible as well. Each of these electrodes 102.*a*, 102.*b* is connected to insulated wires that run inside flexible insulated carriers 103.*a* and 103.*b*.

During implantation, these carriers 103.*a* and 103.*b* are tunneled to the vicinity of the IPG 104, which is typically implanted subcutaneously in the patient's lower abdominal or gluteal region. The proximal ends of the carriers 103.*a* and 103.*b* bear connectors 105.*a* and 105.*b* insertable into a header 104.*a* of the IPG 104 to allow conduction of electrical charge, i.e. the electrical pulses generated in the IPG 104, to the electrodes 102.*a*, 102.*b*. The IPG 104 further comprises a hermetically sealed housing 104.*c* which is e.g. configured such that it may approximate a reference electrode (i.e., an electrode which has a stable and well-known potential, at least over a time window of interest), as by forming it with an effective area and of materials (e.g. fractal Ir or TiN), that make its double-layer capacitance (when implanted) much larger than that of any of the electrodes 102.*a*, 102.*b*.

The IPG 104 may wirelessly communicate with external devices 106 through suitable radio frequency (such as MICS-band or Bluetooth Low Energy), inductive, or any other communication link 107 that allow signal communication through the patient's skin 108. Exemplary external devices 106 may be a clinician programmer 106.*a* and/or a patient remote 106.*b*. The IPG 104 is powered by a battery 104.*b*, which is rechargeable by external means such as via wireless, transcutaneous induction from the external charger 110. The IPG's antenna 112 for wireless communication and a secondary coil 113 are, for example, is embedded in the IPG header 104.*a*, or at least one of them may alternatively be located inside the IPG housing 104.*c*. The external charger 110 comprises a primary coil 110.*a* (see FIG. 2) and may be powered by an internal rechargeable battery to allow patient mobility while charging and/or may be powered directly from the mains power via a power converter (e.g., when its internal battery is low). The charger 110 may itself have only a simple user interface, and it may communicate richer/additional status information for review on a patient remote 106.*b* via an additional wired or wireless communication link 111.

A recharging unit 104.*d* of the IPG 104 includes an LC series resonant circuit, having the secondary coil 113 and capacitors 115.*a* and 115.*b*, to provide current output for recharging the battery 104.*b* upon receipt of an inductive powering link 109. An exemplary operating frequency for inductive battery recharging is 125 kHz. The output of the resonant receiving circuit of the recharging unit 104.*d* is full-wave rectified by rectifying circuit 114 to generate the DC link voltage V_PLnk, which is kept at approximately 4.9 V. Feedback is communicated back to the external charger 110 via the inductive powering link 109 by load shift keying (LSK) as indicated below in detail. The LSK control is implemented in a processing unit 104.*e* provided within the IPG 104. The IPG 104 further comprises a measuring unit (not shown) which measures the actual DC link voltage and/or the battery current ($i_{bat}$) and transmits the actual measurement values to the processing unit 104.*e*. The recharging unit 104.*d* further comprises a charger/management circuit 116 which permits automatic "hot swapping" between the DC link voltage V_PLnk from the rectifying circuit 114 whereby the on-board electronics may be powered while the battery 104.*b* is recharged. The circuitry of the recharging unit 104.*d* further comprises a C-LSK member 125 having a capacitor and a first switch and a R-LSK member 126 having a resistor and a second switch wherein the C-LSK member 125 and the R-LSK member 126 are both connected in parallel to a secondary coil 117 of the recharging unit 104.*d* as shown in FIG. 2. The processing unit 104.*e* is adapted to operatively switch the C-LSK member 125 and the R-LSK member 126, in particular the respective first switch or second switch via a first control connection 125.*a* and a second control connection 126.*a*, respectively.

When the patient is going to recharge the battery 104.*b* of the recharging unit 104.*d* the processing unit 104.*e* triggers measuring the DC link voltage V_PLnk as electrical parameter is of the circuitry by a respective measuring unit which transmits the actual measurement value to the processing unit 104.*e*. Initially, the recharging unit 104.*d* works in the C-LSK mode for recharging the battery 104.*b*. For that, the processing unit 104.*e* switches the first switch of the C-LSK member 125 into a closed configuration. That doesn't necessarily mean that the first (or any another) switch is statically closed. Instead they are operatively modulated (e.g. at 1024 Hz) to perform LSK. Switching from C-LSK to R-LSK just means that the switches to be modulated change. There is no static switch or the switching may be without static switch, in particular it may be dynamically choosing which to excite C-LSK or R-LSK circuits. The second switch of the R-LSK member 126 stays open. The recharging unit 104.*d* receives power for recharging the battery from the electromagnetic field generated by the primary coil 110.*a* of the charger via the secondary coil 117 of the recharging unit 104.*d* and provides feedback communication to the charger 110 using C-LSK. During recharging the DC link voltage is periodically measured by the measurement unit and transmitted to the processing unit 104.*e*. As soon as the measured value of a DC link voltage is out of a pre-defined window or, in one embodiment, the actual measured temperature of the battery is above a maximum value, the processing unit 104.*e* switches the second switch of the R-LSK member 126, i.e. closes this switch, whereas the first switch of the C-LSK member is opened. The recharging unit 104.*d* now operates in the R-LSK mode thereby increasing the amplitude modulation depth. The recharging unit 104.*d* turns back to the C-LSK mode by switching the R-LSK member 126 and the C-LSK member 125. The feedback information is transmitted using amplitude modulation of the charger's driving impedance as explained above. The charger 110 demodulates the signal and digitally restores the contained information as well as executes a pre-defined operation according to the received information, for example shuts the charger 110 off.

In one embodiment two capacitors are switched in parallel by a MOSFET across the IPG resonant tank, and a resistor with MOSFET on VPLNK. The Charger monitor's its coil current or voltage and extracts the AM signal from the carrier.

In another embodiment the recharging unit 104.*d* may additionally toggle R-LSK and C-LSK in the case of a "last gasp" shutdown situation. In this situation a fault of the IPG 104 is detected and the charger 110 shall be shut off. To better improve the reliability of this transmission of LSK messages to the charger 110, the recharging unit 104.*d* sends successive bursts of messages in the C-LSK mode and in the R-LSK mode (for example three in each case) to better improve the chances of communication success.

In another embodiment, the recharging unit 104.*d* may additionally or alternatively provide information to the charger 110 which is used by the charger 110 for maintaining a target supply voltage on the recharging unit 104.*d* of the IPG 104 using a closed-loop control system.

The communication of the IPG 104 and the charger 110 according to the above description is more reliable and allows to use of a single simple amplitude modulation detector on the charger 110. Further, the explained method reduces the size of physical "nulls" whereby the charger 110 is not getting feedback and patient may be notified to re-align (by beeping). The method and the IPG 104 require less hunting around for location where feedback is best observed as well as remove possibilities of cases where purposeful misalignment is required to achieve communication performance.

The invention claimed is:

1. An implantable pulse generator (IPG, 104) for neurostimulation of a patient's body having a recharging unit (104.*d*) with a rechargeable battery (104.*b*) adapted to receive energy from a separate charger (110) utilizing inductive or resonant magnetic power transfer from a primary coil (110.*a*) of the charger to a secondary coil (117) of the recharging unit, wherein the IPG (104) further comprises a processing unit (104.*e*), wherein the recharging unit is adapted to communicate information from the IPG to the charger utilizing capacitive load shift keying (C-LSK) and resistive load shift keying (R-LSK), wherein the processing unit is adapted to control one or both of:

(i) dynamical selection of either C-LSK or R-LSK for communication of a pre-defined information, or (ii) usage of both C-LSK and R-LSK for communication of a pre-defined information in a pre-defined sequence dependent on one or both of:

(A) an actual measured value of at least one parameter of the electric circuitry of the recharging unit, or (B) the type of information which is to be communicated to the charger.

2. The IPG (104) of claim 1, wherein the at least one parameter of the electric circuitry of the recharging unit (104.*d*) is one of: the DC link voltage (V_PLnk) or the battery current ($i_{bat}$).

3. The IPG (104) of claim 1, wherein the IPG further comprises a measurement unit adapted to determine the actual value of the at least one parameter of the electric circuitry and to transmit the measured actual value to the processing unit (104.*e*).

4. The IPG (104) of claim 1, wherein selection of C-LSK comprises switching on a capacitive load connected in parallel to the secondary coil (117) and switching off a resistive load connected in parallel to the secondary coil (117).

5. The IPG (104) of claim 1, wherein selection of R-LSK comprises switching off the capacitive load connected in parallel to the secondary coil (117) and switching on the resistive load connected in parallel to the secondary coil (117).

6. A system (120) comprising the IPG (104) of claim 1 and a separate charger (110) having the primary coil (110.*a*) for providing inductive power transfer to the secondary coil (117).

7. The system (120) of claim 6, wherein the charger is adapted to operate the primary coil (110.*a*) at a constant frequency.

8. A neurostimulation device comprising the IPG (104) of claim 1 and at least one electrode lead (101.*a*, 101.*b*) connected to the IPG (104).

9. A method for operating an implantable pulse generator (IPG, 104) for neurostimulation of a patient's body having a recharging unit (104.*d*) with a rechargeable battery (104.*b*) and a processing unit (104.*e*), wherein the recharging unit receives energy from a separate charger (110) utilizing inductive power transfer from a primary coil (110.*a*) of the charger to a secondary coil (117) of the recharging unit, wherein the recharging unit communicates information from the IPG (104) to the charger utilizing capacitive load shift keying (C-LSK) and resistive load shift keying (R-LSK) by the recharging unit, wherein the processing unit controls one or both of:

(i) a dynamical selection of either C-LSK or R-LSK for communication of a pre-defined information, or (ii) controls a usage of both C-LSK and R-LSK for communication of a pre-defined information in a pre-defined sequence dependent on one or both of:

(A) an actual measured value of at least one parameter of the electric circuitry of the recharging unit, or (B) the type of information which is to be communicated to the charger.

10. The method of claim 9, wherein the at least one parameter of the electric circuitry of the recharging unit (104.*d*) is the DC link voltage (V_PLnk) and the battery current ($i_{bat}$).

11. The method of claim 9, wherein the IPG (104) further comprises a measurement unit which determines the actual value of the at least one parameter of the electric circuitry and transmits the measured actual value to the processing unit (104.*e*).

12. The method of claim 9, wherein selection of C-LSK comprises switching on a capacitive load connected in parallel to the secondary coil (117) and switching off a resistive load connected in parallel to the secondary coil (117).

13. The method of claim 9, wherein selection of R-LSK comprises switching off the capacitive load connected in parallel to the secondary coil (117) and switching on the resistive load connected in parallel to the secondary coil (117).

14. A method for operating a system (120) comprising the IPG (104) and the charger comprising the steps of the method of claim 9, wherein the charger (110) comprises the primary coil (110.*a*) and provides inductive power transfer to the secondary coil (117) of the recharging unit (104.*d*) of the IPG (104).

15. The method of claim 14, wherein the primary coil (110.*a*) operates at a constant frequency.

* * * * *